United States Patent
Kohnle et al.

(10) Patent No.: US 10,821,241 B2
(45) Date of Patent: Nov. 3, 2020

(54) HOUSING FOR AN INHALATION DEVICE AND INHALATION DEVICE FOR ORALLY ADMINISTERING A PHARMACEUTICAL MEDIUM

(71) Applicant: APTAR RADOLFZELL GMBH, Radolfzell (DE)

(72) Inventors: Joerg Kohnle, Villingen-Schwenningen (DE); Frank Keppner, Albstadt (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 827 days.

(21) Appl. No.: 14/906,291

(22) PCT Filed: Jul. 11, 2014

(86) PCT No.: PCT/EP2014/064978
§ 371 (c)(1),
(2) Date: Jan. 20, 2016

(87) PCT Pub. No.: WO2015/010932
PCT Pub. Date: Jan. 29, 2015

(65) Prior Publication Data
US 2016/0166783 A1    Jun. 16, 2016

(30) Foreign Application Priority Data
Jul. 25, 2013   (DE) .................. 10 2013 214 601

(51) Int. Cl.
*A61M 15/00*   (2006.01)
(52) U.S. Cl.
CPC ........ *A61M 15/008* (2014.02); *A61M 15/009* (2013.01); *A61M 15/0021* (2014.02); *A61M 15/0065* (2013.01)

(58) Field of Classification Search
CPC .......... A61M 15/0091; A61M 15/0093; A61M 15/008; A61M 15/0021; A61M 15/009; A61M 15/0068–0083
(Continued)

(56) References Cited

U.S. PATENT DOCUMENTS 5,363,842 A * 11/1994 Mishelevich ........ A61B 8/0875
                                                        128/200.14
5,676,129 A    10/1997 Rocci, Jr. et al.
(Continued)

FOREIGN PATENT DOCUMENTS

DE    10 2010 024 912 A1   12/2011
GB              2470188 A * 11/2010 .......... A61M 15/009
WO       WO 97/33640 A1    9/1997

OTHER PUBLICATIONS

International Search Report issued in Application No. PCT/EP2014/064978 with English translation, dated Oct. 14, 2014 (5 pages).
(Continued)

*Primary Examiner* — Kendra D Carter
*Assistant Examiner* — Elliot S Ruddie
(74) *Attorney, Agent, or Firm* — Flynn Thiel, P.C.

(57) ABSTRACT

A housing for an inhalation device and an inhalation device. The inhalation device includes a container unit having a medium container and an outlet stub. The outlet stub is displaceable relative to the medium container for a delivery operation. The housing includes a main housing having a first end forming a mouthpiece, a second end angled in an L-shaped manner with respect to the first end and forming an air inlet, and an attachment piece. The attachment piece has a duct with an attachment opening receiving the outlet stub of the container unit, a nozzle opening, and a pressure chamber arranged between the attachment opening and the nozzle opening. The housing also includes a sensing device for recording a delivery operation, and a diaphragm revers- (Continued)

ibly deformable depending on a pressure in the pressure chamber. The diaphragm cooperates with the sensing device for actuation thereof.

21 Claims, 1 Drawing Sheet

(58) Field of Classification Search
USPC .................................................. 128/200.23
See application file for complete search history.

(56) References Cited

U.S. PATENT DOCUMENTS

| | | | |
|---|---|---|---|
| 6,138,669 A * | 10/2000 | Rocci, Jr. ............ | A61M 15/009 128/200.14 |
| 8,746,238 B2 | 6/2014 | Kohnle | |
| 2002/0100472 A1 | 8/2002 | Casper et al. | |
| 2007/0017506 A1 * | 1/2007 | Bell .................... | A61M 15/009 128/200.23 |
| 2008/0247965 A1 | 10/2008 | Lewis et al. | |
| 2011/0303221 A1 | 12/2011 | Kohnle | |

OTHER PUBLICATIONS

Written Opinion of International Searching Authority issued in Application No. PCT/EP2014/064978 dated Oct. 14, 2014 (5 pages).

* cited by examiner

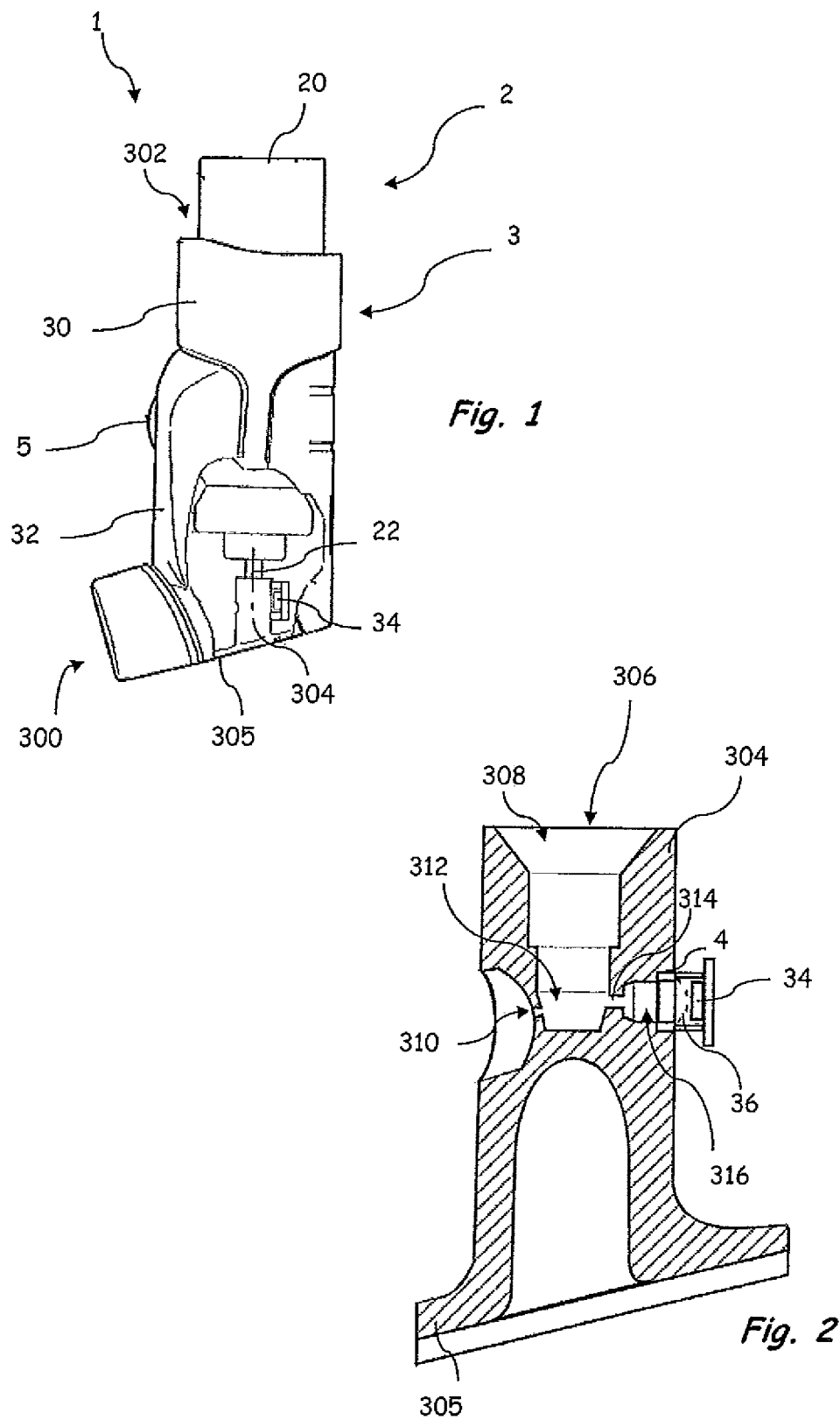

HOUSING FOR AN INHALATION DEVICE AND INHALATION DEVICE FOR ORALLY ADMINISTERING A PHARMACEUTICAL MEDIUM

FIELD OF APPLICATION AND PRIOR ART

The invention relates to a housing for an inhalation device for orally administering a pharmaceutical medium, and to an inhalation device. An inhalation device of the generic type comprises a container unit having a medium container and an outlet stub, wherein the outlet stub is displaceable relative to the medium container for the purposes of a delivery operation. The housing for such an inhalation device comprises a main housing having a first end that forms a mouthpiece, a second end that is angled in an L-shaped manner with respect to the first end and forms an air inlet, and an attachment piece, wherein the attachment piece has a duct with an attachment opening for receiving the outlet stub of the container unit, a nozzle opening that leads out in the direction of the first end, and a pressure chamber arranged between the attachment opening and the nozzle opening. The housing of the generic type furthermore comprises a sensing device for recording a delivery operation.

Inhalation devices of the generic type are usually denoted "MDI" ("Metered-Dose Inhaler") or "pMDI" ("pressurized Metered-Dose Inhaler"). They serve to administer medicines which are intended to pass into the user's lungs in atomized form in order to treat respiratory diseases. They have the abovementioned housing, in which the abovementioned container unit is inserted. The housing has an air inlet that allows air to be drawn into the mouthpiece, wherein, at the same time as the air is drawn in, medium is delivered from the medium container by displacement of the medium container with respect to the outlet stub, such that the drawn-in air mixes with the atomized medium and is breathed in and can thus pass into the lungs.

Medium is delivered from the medium container by the relative displacement of the medium container with respect to the outlet stub. In the simplest case, in inhalation devices of the generic type, the medium container can protrude to a certain extent out of the air inlet of the housing to this end, such that it can be subjected directly to a manual force in order to be displaced with respect to the outlet stub inserted in a corresponding recess in the housing.

In order to give a user of the inhalation device the possibility of quickly and reliably recording the number of doses that still remain in the medium container, what are referred to as delivery sensors for recording individual delivery operations are known.

For this purpose, it is known for example from DE 10 2010 024 912 A1 to provide a housing which has a main portion and a sensor wall portion that is displaceable with respect to the main portion, wherein the sensor wall portion is configured and/or arranged such that, during a delivery operation, it is displaced with respect to the main portion, and wherein the displacement is recordable by a sensing device. In conjunction with the application, sensing device is the name given to an operating element which is actuated by pressing and returns into the starting position following an actuation. In order to return to the starting position, use is made, in advantageous configurations, of a mechanical spring. The use of a sensing device is particularly advantageous on account of the reliability and low production costs. The design known from DE 10 2010 024 912 A1 thus features a simple and thus reliable and cost-effective architecture.

Alternatively, it is known, for example from WO 1997/033640 A1, to arrange a pressure sensor on a duct provided for medium delivery, thereby making the medium delivery recordable. This design is comparatively complex and expensive.

Problem and Solution

The invention addresses the problem of creating a housing for an inhalation device and an inhalation device, by means of which the delivery operations are reliably recordable. In this case, a cost-effective design should in particular also be achieved.

According to a first aspect, a housing for an inhalation device for orally administering a pharmaceutical medium is created, comprising a main housing having a first end that forms a mouthpiece, a second end that is angled in an L-shaped manner with respect to the first end and forms an air inlet, and an attachment piece which has a duct with an attachment opening for receiving the outlet stub of the container unit, with a nozzle opening that leads out in the mouthpiece, and with a pressure chamber arranged between the attachment opening and the nozzle opening, a sensing device for recording a delivery operation, and a diaphragm that is reversibly deformable depending on a pressure in the pressure chamber, said diaphragm cooperating with the sensing device for the actuation thereof.

According to a second aspect, an inhalation device for orally administering a pharmaceutical medium is created, comprising a container unit having a medium container and an outlet stub, and a housing, wherein the housing has a sensing device for recording a delivery operation and a main housing having a first end that forms a mouthpiece, a second end that is angled in an L-shaped manner with respect to the first end and forms an air inlet, and an attachment piece, wherein the attachment piece has a duct with an attachment opening for receiving the outlet stub of the container unit, with a nozzle opening that leads out of the mouthpiece, and with a pressure chamber arranged between the attachment opening and the nozzle opening, and wherein a diaphragm that is reversibly deformable depending on a pressure in the pressure chamber is provided, said diaphragm cooperating with the sensing device for the actuation thereof.

As a result of the medium container being displaced relative to the outlet stub and thus relative to the attachment piece, a puff, or spray, is dispensed. For this purpose, medium is dispensed from the container unit into the pressure chamber, said medium subsequently being delivered in the direction of the mouthpiece via the nozzle opening. On account of the medium in the pressure chamber, a pressure in the pressure chamber rises and the diaphragm is deformed. The deformed diaphragm exerts a pressure on a plunger of the sensing device. A delivery operation is in the process recorded directly on the basis of a pressure rise, associated with the delivery operation, in the pressure chamber.

The diaphragm is made of an elastically deformable material which is suitably selected by a person skilled in the art in accordance with a pressure and/or temperature range specified for the inhalation device. Suitable materials are for example silicone, natural or synthetic polymer dispersions, thermoplastic elastomers or combinations thereof.

In one configuration, the diaphragm is a wall of the pressure chamber. In an advantageous configuration, provision is made for a measuring chamber that is in communication with the pressure chamber and is closed off from the environment by the deformable diaphragm to be provided.

As a result, it is possible to provide the sensing device, which is actuated by the deforming diaphragm, in a spatially separate manner from the pressure chamber. The diaphragm can be configured as a separate component from the remaining components of the housing, said component being joined to said remaining components during assembly. However, a design in which both the diaphragm and surrounding housing parts, which consist of a different and in particular more rigid material, are produced in a common manufacturing process by multicomponent injection-molding is particularly advantageous. As a result, the diaphragm is cohesively connected to the surrounding housing parts.

In one configuration, provision is made for the measuring chamber to be in communication with the pressure chamber via a hole, wherein preferably a diameter of the hole is between about 120% and about 500% of the diameter of the nozzle opening. A diameter of the hole is in this case also dependent on a size of the pressure chamber. Preferably, a diameter of the hole is at most 50% of the diameter of the pressure chamber. In typical configurations, the attachment piece projects from a bottom surface of the main housing, wherein a direction of extension of the attachment piece is parallel to a direction of extension of the main housing in the direction of the second end. In one configuration, the hole extends parallel to the direction of extension of the attachment piece in the direction of the bottom surface of the main housing starting from the pressure chamber. For easy production, the recess, the pressure chamber and a hole connecting the pressure chamber and the measuring chamber are arranged in a manner aligned with one another.

In preferred configurations, the hole branches off from the pressure chamber transversely, preferably substantially perpendicularly to a spraying direction of the container unit, upstream of the nozzle opening in the spraying direction. The nozzle opening and the hole are in this case arranged in a manner offset through about 180° with respect to one another. As a result, a pressure acts on the diaphragm on account of the discharged medium, with the result that the diaphragm is deflected. A pulse force on account of a spray brings about only a slight change, if any, in the deflection on account of the described pressure rise effected by the medium. As a result of this configuration, it is reliably possible to distinguish a complete spray from an incomplete spray, for example on account of incorrect operation.

In a further configuration, provision is made for a recess for forming the measuring chamber to be provided in the attachment piece. The recess for forming the measuring chamber is in this case configured in a manner adjoining a lateral surface of the attachment piece in one configuration.

In one configuration, the main housing is produced as a common injection-molding with the diaphragm, wherein, in one configuration, the diaphragm is introduced as an insert element during the injection-molding of the housing. In advantageous configurations, a holding device having the diaphragm is inserted in the recess. The holding device is designed such that it allows the diaphragm to expand for actuation of the sensing device. Preferably, the holding device is designed such that it allows central expansion of the diaphragm. The shape or design of the holding device is matched to the shape or design of the recess. In advantageous configurations, provision is made of a circular cylindrical recess into which a holding device having an annular cross section is insertable. Such a holding device is mountable easily in the main housing.

In one configuration, the diaphragm is arranged as an insert element in the holding device. In advantageous configurations, the diaphragm and the holding device are manufactured as a one-piece component.

In a further configuration, the sensing device is mounted on the holding device. The sensing device, the diaphragm and the holding device thus form a common structural unit which is mountable on the main housing.

The inhalation device should as a rule be actuated in an upright position. If the inhalation device is actuated in a different orientation, in many cases a dosing chamber of the medium container is not correctly filled and the subsequent spray is incomplete. The diaphragm is preferably designed and/or arranged such that an incomplete spray brings about a different deflection of the diaphragm as compared to a complete spray. According to a first configuration, only a complete spray actuates the sensing device. In advantageous configurations, the sensing device is designed and/or arranged so as to record how strongly and/or how quickly an actuation has taken place. For this purpose, in one configuration, the sensing device comprises two actuating elements arranged in succession. The design allows a distinction to be drawn between a complete spray and incomplete output, wherein both output operations are recorded.

In advantageous configurations, the housing is configured in a multipart manner, comprising the main housing and a cover that is fittable on the main housing and encloses electronic components of a counting unit. The electronic components are in this case arranged in a separate space so as to be protected from access and/or contact with the medium.

BRIEF DESCRIPTION OF THE DRAWINGS

Further advantages and aspects of the invention can be gathered from the claims and from the following description of an exemplary embodiment of the invention, which is explained in the following text by way of the figures, in which:

FIG. 1 schematically shows an inhalation device comprising a container unit and a housing in a partially cut-away side view, and FIG. 2 schematically shows a sectional illustration of a detail of the housing of the inhalation device according to FIG. 1.

DETAILED DESCRIPTION OF THE EXEMPLARY EMBODIMENTS

FIG. 1 schematically shows an inhalation device 1 in a partially cut-away side view. FIG. 2 shows a sectional illustration of a detail according to FIG. 1.

The inhalation device 1 comprises a container unit 2 having a medium container 20 and an outlet stub 22. The inhalation device 1 furthermore comprises a housing 3 having a main housing 30, a cover 32 and a sensing device 34.

The main housing has a first end 300 that forms a mouthpiece, and a second end 302 that is angled in an L-shaped manner with respect to the first end 300 and forms an air inlet. The main housing 30 furthermore comprises an attachment piece 304 which projects in the direction of the second end 302 from a bottom surface 305 of the main housing 30.

As can be seen in FIG. 2, the attachment piece 304 has a duct 306 having an attachment opening 308, a nozzle opening 310 that leads out in the direction of the first end 300 of the main housing 30, and a pressure chamber 312 arranged between the attachment opening 308 and the nozzle opening 310. The attachment opening 308 serves to receive the outlet stub 22 of the container unit 2 according to FIG. 1. The attachment opening 308 and the outlet stub 22 are in this case coordinated with one another such that it is possible for the outlet stub 22 to be received in a clamped manner in the attachment piece 304. The illustration of all the elements, in particular including of the pressure chamber 312, is merely schematic in FIG. 2.

In the exemplary embodiment illustrated, provision is made in the attachment piece 304 of a hole or channel 314 that branches off from the pressure chamber 312 and is located opposite the nozzle opening 310, and of a recess 316 that is arranged in a manner adjoining a lateral surface of the attachment piece 304. In the exemplary embodiment illustrated, the hole 314 is arranged upstream of the nozzle opening 310 in the spraying direction in a manner offset through about 180° with respect to the nozzle opening 310. The recess 316 forms a measuring chamber which is closed off from the environment by a schematically illustrated deformable diaphragm 36. In the exemplary embodiment illustrated, the diaphragm 36 is arranged on a holding device 4 and is mounted in the recess 316 by means of the holding device 4. The measuring chamber 316 is in communication with the pressure chamber 312 via the hole 314 such that a pressure increase in the pressure chamber 312 brings about a pressure increase in the measuring chamber 316.

When the inhalation device 1 is actuated in order to output a spray jet, on account of the medium dispensed from the medium container 20 into the pressure chamber 312, a pressure rise occurs in the pressure chamber 312 and thus also in the measuring chamber 316 which is in communication with the pressure chamber 312 via the hole 314. The pressure increase causes the diaphragm 36 to be deformed, as is illustrated schematically by dashed lines. On account of the deformation of the diaphragm 36, the sensing device 34 is actuated. As a result, a delivery operation is recorded directly, on the basis of the pressure increase, associated with the delivery operation, in the pressure chamber 312. The actuation of the sensing device 34 is processed by means of electronics (not illustrated in the figures) enclosed for example by the cover 32. The electronics are formed in a configuration according to DE 10 2010 024 912 A1, which is hereby incorporated in full by reference.

In the exemplary embodiment illustrated, a display device 5, by means of which the number of recorded delivery operations and/or the number of remaining doses in the medium container 20 are able to be displayed, is furthermore provided on the cover 32.

In the exemplary embodiment illustrated, the hole 314 and the measuring chamber 316—when used properly and when the inhalation device 1 is in an upright orientation as illustrated in FIG. 1—are arranged above the nozzle opening 310 and above an outlet opening of the outlet stub 22. As a result of this arrangement of the hole 314 and the measuring chamber 316, it is possible to record the pressure rise on account of the quantity of delivered medium. A pulse force brought about by the dispensing of the medium into the pressure chamber 312 does not, however, act on the diaphragm 36 or acts thereon only to an insignificant extent. The illustrated arrangement of the measuring chamber 316, of the sensing device 34 and of the diaphragm 36 is thus advantageous, since, as a result of the arrangement, it is possible to reliably distinguish between a complete spray and an incomplete spray. Other designs, in which a sensing device is actuated by means of a reversibly deformable diaphragm, are conceivable, however.

The invention claimed is:

1. A housing for a container unit of an inhalation device for orally administering a pharmaceutical medium, the container unit having a medium container and an outlet stub displaceable relative thereto for the purpose of a delivery operation, said housing comprising:
    a main housing including a first end which forms a mouthpiece and a second end which is angled in a substantially L-shaped manner with respect to said first end and forms an air inlet;
    an attachment piece having a duct with an attachment opening for receiving the outlet stub of the container unit, a nozzle opening that leads outwardly in a direction of said first end, a pressure chamber arranged between said attachment opening and said nozzle opening, a measuring chamber, and a channel disposed to fluidly interconnect said measuring chamber and said pressure chamber, said channel having an upstream end opening into said pressure chamber and a downstream end opening into said measuring chamber;
    a sensing device for recording a delivery operation; and
    a diaphragm which is reversibly deformable in response to fluid entering said measuring chamber from said pressure chamber via said channel, said diaphragm being disposed to cooperate with said sensing device such that deformation of said diaphragm due to fluid in said measuring chamber actuates said sensing device, said diaphragm in its entirety being spaced from each of said pressure chamber and said downstream end of said channel.

2. The housing according to claim 1, wherein said channel has a diameter between about 120% and about 500% of a diameter of said nozzle opening.

3. The housing according to claim 1, wherein said pressure chamber is oriented along an axis substantially parallel to a direction of discharge of pharmaceutical medium into said pressure chamber, said channel has an axis oriented transversely relative to the axis of said pressure chamber, and said measuring chamber has an axis oriented transversely relative to the axis of said pressure chamber and substantially parallel to the axis of said channel.

4. The housing according to claim 1, wherein said measuring chamber is interposed between said pressure chamber and said diaphragm.

5. The housing according to claim 4, wherein said measuring chamber is in fluid communication with said nozzle opening via said pressure chamber, and said pressure chamber opens directly into said nozzle opening.

6. The housing according to claim 1, wherein said attachment piece further includes a recess therein which defines part of said measuring chamber, said housing further including a holding device for said diaphragm disposed within said recess.

7. The housing according to claim 6, wherein said holding device and said diaphragm are constructed as a one-piece component.

8. The housing according to claim 6, wherein said sensing device is mounted on said holding device and is configured to record how strongly and/or how quickly an actuation has taken place.

9. The housing according to claim 1, wherein said housing is configured as a multi-part component and further includes a cover configured for fitting on said main housing and configured for enclosing electronics of a counting unit.

10. The housing according to claim 1, wherein said pressure chamber at one side thereof opens directly into said nozzle opening and at an opposite side opens directly into said upstream end of said channel, said downstream end of said channel opening directly into said measuring chamber, and said diaphragm is disposed immediately adjacent said measuring chamber.

11. The housing according to claim 1, wherein said upstream end of said channel has a cross-section less than a cross-section of said pressure chamber disposed immediately adjacent said upstream end, and said downstream end of said channel having a cross-section less than a cross-section of said measuring chamber disposed immediately adjacent said downstream end of said channel.

12. A housing for an inhalation device for orally administering a pharmaceutical medium including a medium container and an outlet stub displaceable relative thereto to cause a delivery operation, said housing comprising:
   a first housing part having a first housing portion defining a mouthpiece through which pharmaceutical medium is discharged and a second housing portion oriented transversely relative to said first housing portion and defining an air inlet;
   a second housing part having a duct configured for receiving therein the outlet stub of the medium container, a nozzle opening oriented in a direction of said mouthpiece, a pressure chamber disposed between said duct and said nozzle opening, a measuring chamber, and a channel disposed to fluidly interconnect said measuring chamber and said pressure chamber and having a first end opening into said pressure chamber and a second end opening into said measuring chamber, said channel having a diameter less than a diameter of each of said pressure chamber and said measuring chamber;
   a sensing device configured to record a delivery operation; and
   a resiliently deflectable diaphragm, wherein an increase in pressure in said pressure chamber due to fluid entering said pressure chamber causes an increase in pressure in said measuring chamber, and an increase in pressure in said measuring chamber deflects said diaphragm and actuates said sensing device, said diaphragm being disposed in said measuring chamber and said diaphragm being spaced from and not in contact with said second end of said channel, said measuring chamber having a chamber portion unoccupied by said diaphragm between said second end of said channel and said diaphragm and into which chamber portion fluid enters from said pressure chamber via said channel.

13. The housing according to claim 12, wherein said pressure chamber opens directly into said nozzle opening and is disposed to permit fluid communication between the outlet stub of the medium container, when disposed in said duct, and said nozzle opening.

14. The housing according to claim 12, wherein said sensing device and said diaphragm are mounted on said second housing part.

15. The housing according to claim 14, wherein said second housing part is mounted within an interior of said first housing part and said second housing part has a recess therein which defines part of said measuring chamber, said diaphragm being disposed in said recess to seal off said measuring chamber from said interior of said first housing part.

16. The housing according to claim 12, wherein said diaphragm in its entirety is spaced from said pressure chamber.

17. An inhalation device for orally administering a pharmaceutical medium, said inhalation device comprising:
   a container unit including a medium container and an outlet stub in fluid communication with said medium container and displaceable relative thereto for the purpose of a discharge operation of said inhalation device;
   a housing, said container unit being disposed within said housing, said housing comprising:
      a first housing part including a first housing portion having a mouthpiece through which pharmaceutical medium is discharged to a user and a second housing portion having an air inlet, said second housing portion being oriented transversely relative to said first housing portion; and
      a second housing part including a duct, said outlet stub of said container unit being disposed within said duct, said second housing part further including a nozzle opening oriented to direct pharmaceutical medium towards said mouthpiece, a pressure chamber disposed in fluid communication with said outlet stub and said nozzle opening, a measuring chamber, a channel interposed between said pressure chamber and said measuring chamber to fluidly interconnect said measuring chamber and said pressure chamber, said channel being connected to said pressure chamber at a first junction and being connected to said measuring chamber at a second junction, said channel having a cross-section at each of said first and second junctions, said pressure chamber having a cross-section at said first junction and said measuring chamber having a cross-section at said second junction, said cross-section of said channel at said first junction being less than said cross-section of said pressure chamber, and said cross-section of said channel at said second junction being less than said cross-section of said measuring chamber, and a resiliently deformable diaphragm disposed adjacent said measuring chamber, said diaphragm being spaced from said second junction;
   a sensing device configured to record a discharge operation of said inhalation device, wherein fluid entering said measuring chamber from said pressure chamber via said channel during a discharge operation of said inhalation device causes deformation of said diaphragm to actuate said sensing device.

18. The inhalation device according to claim 17, wherein said channel is disposed upstream, with respect to a fluid flow direction through said inhalation device, of said nozzle opening.

19. The inhalation device according to claim 17, wherein said sensing device is mounted on said second housing part.

20. The inhalation device according to claim 19, wherein said second housing part is mounted within an interior of said first housing part and said second housing part has a recess therein which partially defines said measuring chamber, said diaphragm being disposed in said recess and sealing off said measuring chamber from said interior of said first housing part.

21. The inhalation device according to claim 17, wherein said diaphragm is disposed immediately adjacent said measuring chamber, said diaphragm in its entirety being spaced from said pressure chamber.

* * * * *